(12) United States Patent
Matsumoto et al.

(10) Patent No.: US 8,568,578 B2
(45) Date of Patent: Oct. 29, 2013

(54) ELECTRODE FOR ELECTROCHEMICAL MEASUREMENT APPARATUS AND ELECTRODE FOR BIOSENSOR

(75) Inventors: Toru Matsumoto, Minato-ku (JP); Naoaki Sata, Minato-ku (JP); Yoko Mitarai, Tsukuba (JP)

(73) Assignees: NEC Corporation, Tokyo (JP); National Institute for Materials Science, Ibaraki (JP)

( * ) Notice: Subject to any disclaimer, the term of this patent is extended or adjusted under 35 U.S.C. 154(b) by 456 days.

(21) Appl. No.: 12/741,158

(22) PCT Filed: Oct. 29, 2008

(86) PCT No.: PCT/JP2008/070156
§ 371 (c)(1),
(2), (4) Date: May 3, 2010

(87) PCT Pub. No.: WO2009/060878
PCT Pub. Date: May 14, 2009

(65) Prior Publication Data
US 2010/0258452 A1    Oct. 14, 2010

(30) Foreign Application Priority Data

Nov. 7, 2007 (JP) ................................. 2007-289836

(51) Int. Cl.
*G01N 27/327* (2006.01)
*G01N 1/00* (2006.01)
*G01N 27/26* (2006.01)
*C12M 1/00* (2006.01)

(52) U.S. Cl.
USPC ................. 204/403.01; 204/403.14; 204/400; 205/775; 205/777.5; 205/782

(58) Field of Classification Search
USPC ................ 204/403.01–403.15, 400; 205/775, 205/777.5, 792
See application file for complete search history.

(56) References Cited

U.S. PATENT DOCUMENTS

| | | | | |
|---|---|---|---|---|
| 2,802,894 A | * | 8/1957 | Schneider et al. | ............. 136/232 |
| 5,922,183 A | * | 7/1999 | Rauh | ......................... 204/403.1 |
| 6,869,328 B2 | * | 3/2005 | Ulm et al. | ......................... 445/7 |
| 2007/0056852 A1 | * | 3/2007 | Kubo et al. | .............. 204/403.14 |

FOREIGN PATENT DOCUMENTS

| | | |
|---|---|---|
| JP | 01-153952 A | 6/1989 |
| JP | 08-240562 A | 9/1996 |
| JP | 09-127053 A | 5/1997 |
| JP | 2000-081409 A | 3/2000 |

(Continued)

OTHER PUBLICATIONS

Faming Tian et al., "Sol-gel derived iridium composite glucouse biosensor," Sensors and Actuators B: Chemical, Elsevier B.V, (Netherlands), Sep. 2002, vol. 86, pp. 266-270.

(Continued)

*Primary Examiner* — Alex Noguerola
*Assistant Examiner* — Maris R Kessel
(74) *Attorney, Agent, or Firm* — Sughrue Mion, PLLC

(57) ABSTRACT

An object of the present invention is to provide an electrode for an electrochemical measurement apparatus that is less susceptible to influence from interference substances as compared to conventional technology and an electrochemical measurement apparatus using such an electrode. A working electrode 9 (an electrode 1 for an electrochemical measurement apparatus) used in an electrochemical measurement apparatus 3 of the present invention uses an alloy containing iridium and rhenium with such a composition that selectivity for hydrogen peroxide can be obtained.

16 Claims, 5 Drawing Sheets

(56) References Cited

FOREIGN PATENT DOCUMENTS

| | | |
|---|---|---|
| JP | 2001-116716 A | 4/2001 |
| JP | 3854892 B2 | 12/2002 |
| JP | 2003-121407 A | 4/2003 |

OTHER PUBLICATIONS

Shen, Jie, et al., "An iridium nanoparticles dispersed carbon based thick film electrochemical biosensor and its application for a single use, disposable glucose biosensor", ScienceDirect, Sensors and Actuator B 125, 2007, pp. 106-113.

* cited by examiner

ELECTRODE FOR ELECTROCHEMICAL MEASUREMENT APPARATUS AND ELECTRODE FOR BIOSENSOR

BACKGROUND OF THE INVENTION

The present invention relates to an electrode for an electrochemical measurement apparatus, an electrochemical measurement apparatus using an electrode for an electrochemical measurement apparatus, an electrode for a biosensor, a biosensor using an electrode for a biosensor, a method of manufacturing an electrode for an electrochemical measurement apparatus, a method of manufacturing an electrode for a biosensor, a measurement method using an electrochemical measurement apparatus, and a measurement method using a biosensor.

Various devices for measuring the concentration of hydrogen peroxide in a solution are widely used to measure the concentration of hydrogen peroxide contained in a reducing agent used in a semiconductor fabrication process, to measure the concentration of hydrogen peroxide contained in a fungicide solution or an antiseptic solution used in a food manufacturing process, or to measure the concentration of hydrogen peroxide in water of a nuclear reactor.

Examples of a device for measuring the concentration of hydrogen peroxide in a solution include a device using an electrochemical reaction. Electrodes are immersed in a solution containing hydrogen peroxide. Carbon electrodes or electrodes of a noble metal such as platinum are used. Measurement is performed by detecting an electric current flowing when electric potential is applied.

This is because hydrogen peroxide is oxidized on a surface of the electrode to produce an oxidation current. Therefore, the concentration of hydrogen peroxide in the solution can be measured by measuring the oxidation current.

Meanwhile, measurement equipments in which a catalytic reaction of protein and an electrochemical reaction are combined with each other in addition to the aforementioned electrochemical reaction of hydrogen peroxide are widely used as a device for measuring the concentration of a substance contained in a variety of solutions.

Furthermore, there have been generalized a biosensor that converts a chemical substance in a solution into hydrogen peroxide by a catalytic function of an enzyme and measures the converted hydrogen peroxide with an oxidation-reduction reaction using the aforementioned electrodes. There have also been generalized an immunological sensor that allows a chemical substance (antigen) in a solution to react with an antibody and measures the concentration of the chemical substance in the solution by detecting an electric current produced by the reaction.

For example, if glucose is oxidized by glucose oxidase, gluconolactone and hydrogen peroxide are generated. The amount of hydrogen peroxide generated is in proportion to the concentration of the glucose.

Electrodes in which glucose oxidase has been immobilized on a surface of an electrode on which hydrogen peroxide is to be oxidized are prepared as electrodes used for a glucose biosensor. When those electrodes are immersed in a solution, the glucose oxidase oxidizes glucose, so that gluconolactone and hydrogen peroxide are generated.

Since the generated hydrogen peroxide is oxidized on the surface of the electrode, the concentration of the glucose in a sample can be measured by measuring an electric current produced by the oxidation.

Here, noble metals, which have higher oxidizability to hydrogen peroxide than other electrode materials, are used for the electrode for detecting hydrogen peroxide.

For example, Japanese laid-open patent publication No. 2001-116716 (Patent Document 1) and Japanese laid-open patent publication No. 2000-81409 (Patent Document 2) describe that platinum is preferably used as such an electrode material.

Meanwhile, platinum is expensive as an electrode material and has less workability as compared to other electrode materials. Therefore, electrode materials using substances other than platinum are used in some cases.

For example, Faming Tian and Guoyi Zhu, "Sol-gel derived iridium composite glucouse biosensor," Sensors and Actuators B: Chemical, Elsevier B.V, (Netherlands), Volume 86, September 2002, pp. 266-270 (Non-Patent Document 1) discloses an electrode using iridium oxide.

Furthermore, Japanese patent No. 3854892 (Patent Document 3) discloses that iridium is one of preferable materials.

Those electrodes are used to measure the concentration of glucose by measuring an electric current after electric potential is applied to hydrogen peroxide.

DISCLOSURE OF INVENTION

The aforementioned electrodes using noble metals or iridium oxide are useful for an electrode for detecting hydrogen peroxide, an electrochemical measurement apparatus using such an electrode, and an electrode for a biosensor.

However, it is preferable for those electrodes to have structure and composition that can avoid influence from substances other than hydrogen peroxide contained in a solution as much as possible.

Specifically, when hydrogen peroxide is oxidized on a surface of an electrode, other substances in a solution may simultaneously be oxidized as interference substances, which produce a current output such that the measurement precision is lowered. Therefore, countermeasures for this problem should be taken.

For example, ascorbic acid (a.k.a. vitamin C), urate, acetaminophen, and the like act as an interference substance on an electrode for detecting a current or an electrode for a biosensor that has been produced by using platinum or iridium as an electrode material. Therefore, countermeasures for this problem should be taken.

On the other hand, in a case of a glucose biosensor that has been produced by using iridium oxide as an electrode material, a current output is lowered with respect to those interference substances but is not sufficiently lowered.

Furthermore, an applied potential should be set at 0 V or less. The electrode is likely to be influenced by oxygen in a solution. Therefore, other countermeasures for interference substances should be taken.

Moreover, the electrode is susceptive to influence of the self-potential of the electrode in the case where an applied potential is near 0 V. Therefore, the measurement precision, particularly the measurement precision in repeatability, may be lowered.

The present invention has been made for the above reasons. It is, therefore, an object of the present invention to provide an electrode for an electrochemical measurement apparatus that is less susceptible to influence from interference substances as compared to conventional technology and an electrochemical measurement apparatus (biosensor) using such an electrode.

In order to achieve the aforementioned object, a first invention provides an electrode for an electrochemical measurement apparatus to detect hydrogen peroxide in a solution, being formed of an alloy containing at least iridium and rhenium with such a composition that selectivity for hydrogen peroxide can be obtained.

A second invention provides an electrode for an electrochemical measurement apparatus to detect hydrogen peroxide in a solution, being formed of an alloy containing at least iridium and rhenium so that an atom weight ratio of iridium and rhenium is in a range of from 99:1 to 50:50.

A third invention provides an electrochemical measurement apparatus for measuring a concentration of hydrogen peroxide in a solution, comprising the electrode for an electrochemical measurement apparatus as recited in the first invention or the second invention.

A fourth invention provides an electrode for a biosensor to detect a measurement target substance in a solution, wherein an immobilized enzyme layer and/or an immobilized antibody layer is provided on a surface of the electrode for an electrochemical measurement apparatus as recited in the first invention or the second invention.

A fifth invention provides a biosensor for measuring a concentration of a measurement target substance in a solution, comprising the electrode for a biosensor as recited in the fourth invention.

A sixth invention provides a method of manufacturing an electrode for an electrochemical measurement apparatus to detect hydrogen peroxide in a solution, comprising a process of manufacturing, by one of an arc-melting method, a vapor deposition method, and a sputtering method, an alloy containing at least iridium and rhenium with such a composition that selectivity for hydrogen peroxide can be obtained.

A seventh invention provides a method of manufacturing an electrode for a biosensor to detect a measurement target substance in a solution, comprising a process of providing an immobilized enzyme layer and/or an immobilized antibody layer on a surface of the electrode for an electrochemical measurement apparatus as recited in the first invention or the second invention.

An eighth invention provides a measurement method using the electrochemical measurement apparatus as recited in the third invention to measure a concentration of hydrogen peroxide in a solution by a current detection method.

A ninth invention provides a measurement method using the biosensor as recited in the fifth invention to measure a concentration of a measurement target substance in a solution by a current detection method.

EFFECTS OF THE INVENTION

According to the present invention, there can be provided an electrode for an electrochemical measurement apparatus that is less susceptible to influence from interference substances as compared to conventional technology and an electrochemical measurement apparatus (biosensor) using such an electrode.

BRIEF DESCRIPTION OF DRAWINGS

FIG. 2A is a schematic view showing a biosensor 3a.

DESCRIPTION OF REFERENCE NUMERALS

Figure 1:
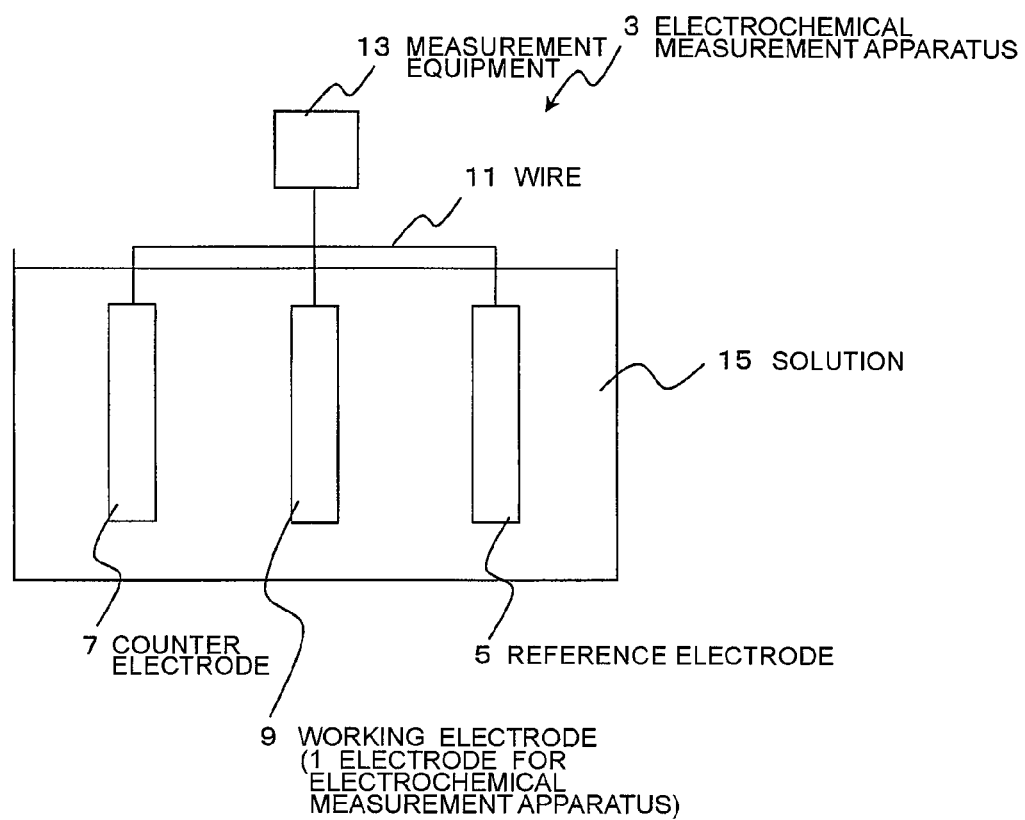
FIG. 1 is a schematic view showing an electrochemical measurement apparatus 3.

1 Electrode for electrochemical measurement apparatus
3 Electrochemical measurement apparatus
3a Biosensor
3b Biosensor
4 Electrode for biosensor
5 Reference electrode
6 Immobilized enzyme layer (immobilized antibody layer)
7 Counter electrode
9 Working electrode
11 Wire
13 Measurement device
15 Solution
23 Insulating substrate
24 Binder layer

BEST MODE FOR CARRYING OUT THE INVENTION

Preferred embodiments of the present invention will be described in detail based on the drawings.

First, a configuration of an electrochemical measurement apparatus 3 having an electrode 1 for an electrochemical measurement apparatus according to a first embodiment of the present invention will be described with reference to FIG. 1.

Here, an electrochemical measurement apparatus for measuring the concentration of hydrogen peroxide in a solution 15 is illustrated as the electrochemical measurement apparatus 3.

The electrochemical measurement apparatus 3 shown in FIG. 1 includes a working electrode 9 (the electrode 1 for an electrochemical measurement apparatus) for oxidizing hydrogen peroxide in the solution 15, a reference electrode 5 for providing a reference potential, and a counter electrode 7 provided as needed.

Furthermore, the electrochemical measurement apparatus 3 also includes a measurement equipment 13 for controlling application of a potential during the measurement or the like and measuring an oxidation current so as to measure the concentration of hydrogen peroxide and wires 11 connecting the electrodes to the measurement equipment 13.

The electrochemical measurement apparatus 3 measures the concentration of hydrogen peroxide in the solution 15 by immersing the working electrode 9, the counter electrode 7, and the reference electrode 5 in the solution 15 containing hydrogen peroxide, applying a constant potential via the measurement equipment 13, and measuring a value of an oxidation current produced when hydrogen peroxide is oxidized on a surface of the working electrode 9.

Specifically, the electrochemical measurement apparatus 3 measures the concentration of hydrogen peroxide in the solution by a current detection method.

Here, it is preferable for the working electrode 9 to be formed by structure and material that are unlikely to be influenced by interference substances during the measurement as described above.

In other words, it is preferable for the working electrode 9 to have such selectivity as to oxidize only hydrogen peroxide during the measurement.

The inventors have diligently studied the above problems and found that an electrode can be made less susceptive to influence from interference substances by using an alloy containing at least iridium and rhenium with such a composition that the selectivity for hydrogen peroxide can be obtained.

Substances of the alloy will be described in greater detail.

Iridium has high oxidizability to hydrogen peroxide. Furthermore, iridium is less expensive and has higher workability as compared to gold or platinum, which has heretofore been used as a material for a working electrode. Iridium is essential for oxidizing hydrogen peroxide in the solution 15.

Rhenium has oxidizability to hydrogen peroxide. Furthermore, rhenium is an element for providing an electrode with the selectivity for hydrogen peroxide when it is added to iridium. Rhenium is essential for making an electrode less susceptive to influence from interference substances as compared to conventional technology.

However, if a ratio of rhenium to iridium in the alloy is equal to or less than 1 atom weight %, then the selectivity cannot be provided sufficiently.

Therefore, a ratio of rhenium to iridium in the alloy is preferably in a range of 1 atom weight % to 50 atom weight %, or an atom weight ratio of iridium and rhenium is preferably in a range of 99:1 to 50:50.

More preferably, an atom ratio of rhenium to iridium is in a range of 1 atom weight % to 10 atom weight %, or an atom weight ratio of iridium and rhenium is preferably in a range of 99:1 to 90:10.

The alloy may be formed of iridium and rhenium only. In such a case, an atom weight ratio of iridium and rhenium is preferably in a range of 99:1 to 50:50.

Specifically, the electrode is formed of an iridium-rhenium alloy, and a rhenium content is in a range of 1 atom weight % to 50 atom weight %.

In this case, a preferable range of the atom weight ratio of iridium and rhenium is from 99:1 to 90:50.

For example, the alloy is produced by an arc-melting method, a vapor deposition method, or a sputtering method. It is preferable to produce the alloy by an arc-melting method because materials can be used efficiently.

Any known electrodes can be used for the reference electrode 5. Examples of such electrodes include a glass composite electrode.

Furthermore, any known electrodes can be used for the counter electrode 7. Examples of such electrodes include a platinum electrode.

Here, a method of measuring the concentration of hydrogen peroxide in the solution 15 with the electrochemical measurement apparatus 3 will be described in detail.

First, the working electrode 9, the counter electrode 7, and the reference electrode 5 are immersed in the solution 15 containing hydrogen peroxide.

For example, the solution 15 is a reducing agent used in a semiconductor fabrication process, a fungicide solution or an antiseptic solution used in a food manufacturing process, or water of a nuclear reactor.

When those electrodes are immersed in the solution 15, a constant potential is applied with the measurement equipment 13.

Hydrogen peroxide is oxidized on the surface of the working electrode 9 by application of the potential, so that an oxidation current is produced.

The measurement equipment 13 measures the oxidation current. Based on the measured value, the measurement equipment 13 measures the concentration of hydrogen peroxide in the solution 15.

As described above, the working electrode 9 employs an alloy containing iridium and rhenium with such a composition that the selectivity for hydrogen peroxide can be obtained.

With this configuration, even if the solution 15 includes interference substances such as a uric acid, an ascorbic acid, or other organic acids, the interference substances can be prevented from being oxidized on the surface of the working electrode 9 as compared to conventional technology. Therefore, it is possible to prevent a current output caused by oxidation of the interference substances and thus prevent reduction of the measurement precision.

In other words, the measurement precision for the concentration of hydrogen peroxide in the solution 15 can be improved as compared to conventional technology.

Thus, according to the first embodiment, the electrochemical measurement apparatus 3 includes the working electrode 9, the counter electrode 7, the reference electrode 5, and the measurement equipment 13. The working electrode 9 employs an alloy containing iridium and rhenium with such a composition that the selectivity for hydrogen peroxide can be obtained.

Accordingly, even if the solution 15 includes interference substances, the interference substances can be prevented from being oxidized on the surface of the working electrode 9 as compared to conventional technology. Therefore, it is possible to prevent a current output caused by oxidation of the interference substances and thus prevent reduction of the measurement precision.

In other words, the working electrode 9 is less susceptive to influence from interference substances as compared to conventional technology.

Next, a second embodiment will be described with reference to FIGS. 2A and 2B.

The second embodiment differs from the first embodiment in that a working electrode 9a is formed by an electrode 4 for a biosensor, which has a surface covered with an immobilized enzyme layer 6, and that the entire apparatus constitutes a biosensor 3a.

In the second embodiment, elements that demonstrate the same effects as in the first embodiment are denoted by the same reference numerals, and the explanation thereof is omitted herein.

Figure 2A:
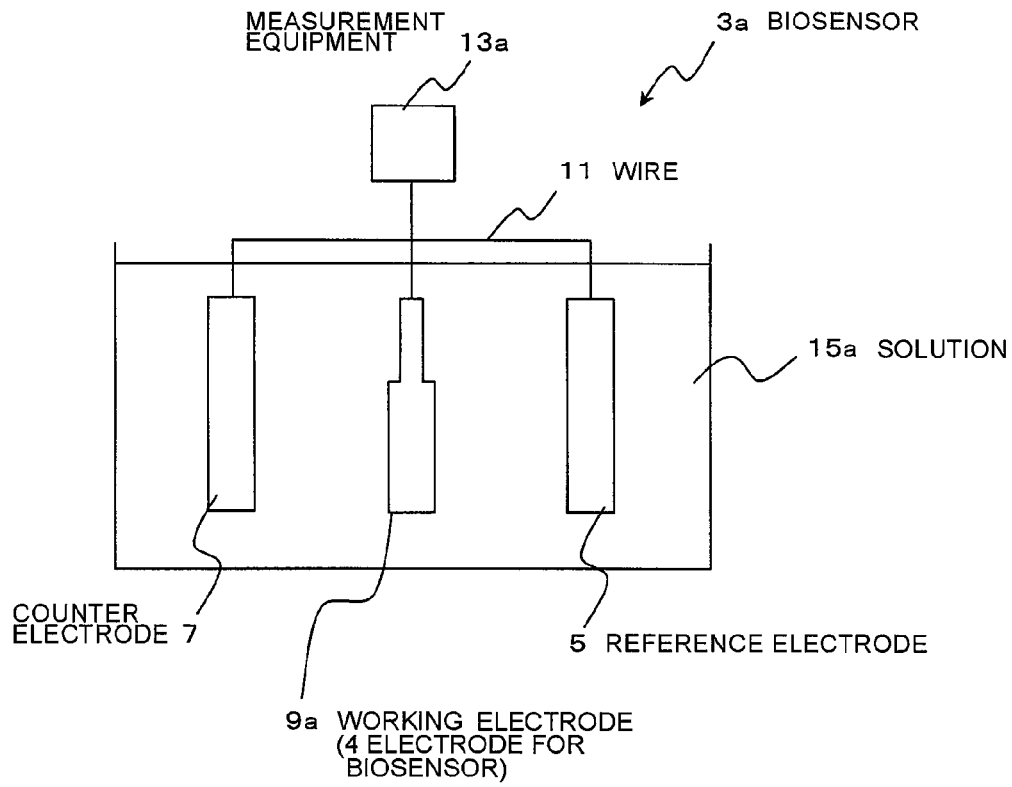

As shown in FIG. 2A, the biosensor 3a has the same configuration as the electrochemical measurement apparatus 3. However, the biosensor 3a has the working electrode 9a (the electrode 4 for a biosensor) for converting a measurement target substance in the solution 15a into hydrogen peroxide and oxidizing the resultant hydrogen peroxide.

Furthermore, the biosensor 3a also has a measurement equipment 13a for controlling application of a potential during the measurement or the like, measuring an oxidation current so as to measure the concentration of hydrogen peroxide, and measuring the concentration of the measurement target substance based on the measured concentration of hydrogen peroxide.

Figure 2B:
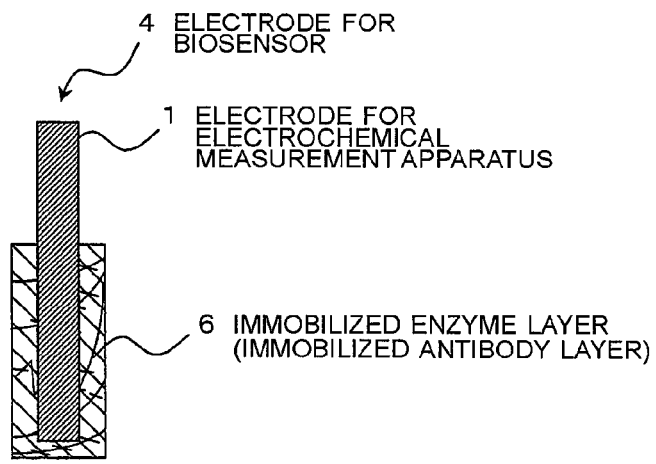
FIG. 2B is a vertical cross-sectional view showing a working electrode 9a (an electrode 4 for a biosensor) of FIG. 2A.

As shown in FIG. 2B, the electrode 4 for a biosensor includes the electrode 1 for an electrochemical measurement apparatus and the immobilized enzyme layer 6 (or an immobilized antibody layer) provided on a surface of the electrode 1 for an electrochemical measurement apparatus to convert the measurement target substance into hydrogen peroxide.

The structure and composition of the electrode 1 for an electrochemical measurement apparatus are the same as those of the electrode 1 for an electrochemical measurement apparatus according to the first embodiment. The electrode 1 for an electrochemical measurement apparatus employs an alloy containing iridium and rhenium with such a composition that the selectivity for hydrogen peroxide can be obtained.

The immobilized enzyme layer 6 is a layer containing an enzyme that converts the measurement target substance into hydrogen peroxide.

The biosensor 3a can measure the concentration of the measurement target substance in the solution 15a by converting the measurement target substance into hydrogen peroxide with the enzyme of the immobilized enzyme layer 6 and measuring an oxidation current produced when the resultant hydrogen peroxide is oxidized on a surface of the electrode 1 for an electrochemical measurement apparatus.

Specifically, the biosensor 3a measures the concentration of the measurement target substance in the solution by measuring the concentration of hydrogen peroxide in the solution by a current detection method.

The enzyme should generate hydrogen peroxide as a product of a catalytic reaction of the measurement target substance or should consume oxygen. Lactate oxidase, glucose oxidase, uric acid oxidase, urea oxidase, alcohol oxidase, and the like are used as the enzyme depending upon the measurement target substance.

Furthermore, two or more kinds of enzymes may be used simultaneously. For example, creatininase, creatinase, and sarcosine oxidase may be used for this purpose.

Creatinine can be detected by using such an enzyme.

Furthermore, the immobilized enzyme layer 6 may include an enzyme and a coenzyme.

Any known methods can be used to immobilize an enzyme on a surface of the electrode 1 for an electrochemical measurement apparatus. Examples of those known methods include a method using a crosslinking reaction.

Specifically, an enzyme is immobilized on a surface of the electrode 1 for an electrochemical measurement apparatus by dropping an enzyme solution, a crosslinking agent of protein such as glutaraldehyde, and a solution containing albumin onto the surface of the electrode 1 for an electrochemical measurement apparatus. Thus, the immobilized enzyme layer 6 is formed.

As described above, the immobilized enzyme layer 6 is not specifically limited as long as it includes at least an enzyme and has a function of converting the measurement target substance into hydrogen peroxide.

When an immobilized antibody layer is used instead of the immobilized enzyme layer 6, an antibody such as a chorionic gonadotropin antibody is used depending upon the measurement target substance.

For example, an antibody is immobilized as follows: The electrode 1 for an electrochemical measurement apparatus is immersed in a solution containing the antibody for a predetermined period of time. Then, the electrode is swept in a phosphate buffer solution containing sodium chloride for thereby immobilizing the antibody to form an immobilized antibody layer.

The immobilized antibody layer may be covered with polyvinyl alcohol as needed for preventing separation of the antibody and immobilizing the antibody more firmly.

When an immobilized antibody layer is thus provided instead of the immobilized enzyme layer 6, the biosensor 3a serves as an immunological sensor.

Here, a method of measuring the concentration of the measurement target substance in the solution 15a with the biosensor 3a will be described in detail.

First, the working electrode 9a, the counter electrode 7, and the reference electrode 5 are immersed in the solution 15a containing the measurement target substance.

For example, the solution 15a is urine of a diabetic patient in a case where the measurement target substance is glucose or is urine of a woman who may be pregnant in a case where the measurement target substance is chorionic gonadotropin.

When those electrodes are immersed in the solution 15a, a constant potential is applied with the measurement equipment 13a.

If the biosensor 3a is an enzyme sensor using the immobilized enzyme layer 6, the measurement target substance in the solution 15a is brought into contact with the immobilized enzyme layer 6 of the working electrode 9a and converted into hydrogen peroxide by a catalytic reaction when the electrodes are immersed in the solution 15a.

The resultant hydrogen peroxide is oxidized on the surface of the electrode 1 for an electrochemical measurement apparatus in the working electrode 9a by application of the potential, so that an oxidation current is produced.

The measurement equipment 13a measures the oxidation current. Based on the measured oxidation current, the measurement equipment 13a measures the concentration of hydrogen peroxide.

Furthermore, based on the measured concentration of hydrogen peroxide, the measurement equipment 13a measures the concentration of the measurement target substance in the solution 15a.

In a case where the biosensor 3a is an immunological sensor, the antibody reacts with the measurement target substance when the electrodes are immersed in the solution 15a. Therefore, a current value caused by the reaction is measured with the measurement equipment 13a by a square wave voltammetry method. The concentration of the measurement target substance in the solution 15a is measured based on the current value.

As described above, the electrode 1 for an electrochemical measurement apparatus in the working electrode 9a employs an alloy containing iridium and rhenium with such a composition that the selectivity for hydrogen peroxide can be obtained.

With this configuration, even if the solution 15a includes interference substances such as an ascorbic acid or acetaminophen, the interference substances can be prevented from being oxidized on the surface of the electrode 1 for an electrochemical measurement apparatus as compared to conventional technology. Therefore, it is possible to prevent a current output caused by oxidation of the interference substances and thus prevent reduction of the measurement precision.

In other words, the measurement precision for the measurement target substance can be improved as compared to conventional technology.

Thus, according to the second embodiment, the biosensor 3a includes the working electrode 9a, the counter electrode 7, the reference electrode 5, and the measurement equipment 13a. The electrode 1 for an electrochemical measurement apparatus in the working electrode 9a employs an alloy containing iridium and rhenium with such a composition that the selectivity for hydrogen peroxide can be obtained.

Accordingly, it is possible to obtain the same advantages as in the first embodiment.

Next, a third embodiment will be described with reference to FIGS. 3 and 4.

A biosensor 3b of the third embodiment includes a working electrode 25a (electrode 4a for a biosensor) in which the electrode 1 for an electrochemical measurement apparatus is provided on an insulating substrate 23 while a binder layer 24 is further provided between the electrode 1 for an electrochemical measurement apparatus and the immobilized enzyme layer 6 in the second embodiment.

Figure 3:
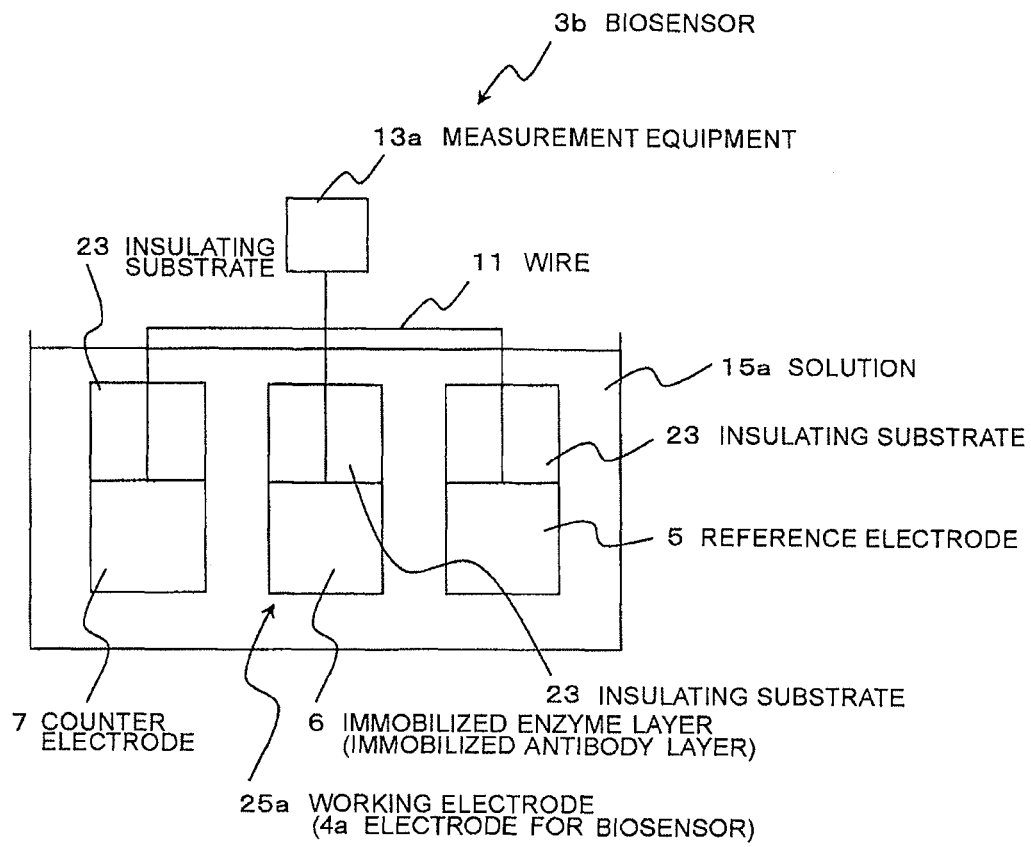
FIG. 3 is a schematic view showing a biosensor 3b.
Figure 4:
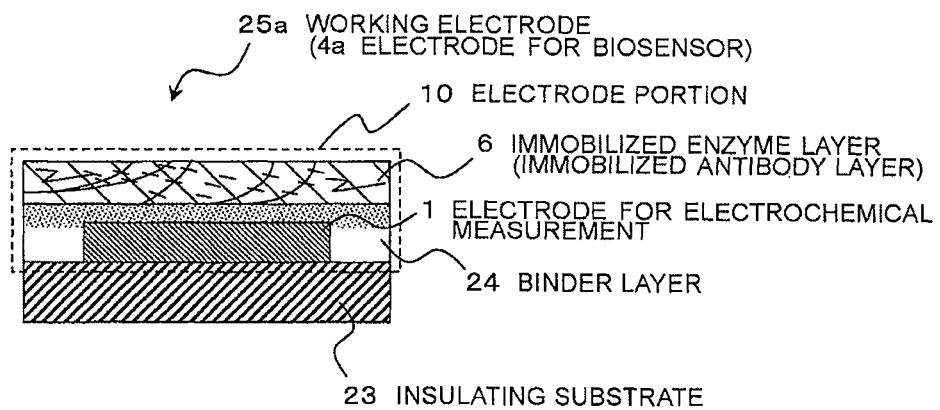
FIG. 4 is a cross-sectional view of an electrode 4a for a biosensor in FIG. 3.

As shown in FIGS. 3 and 4, the working electrode 25a (the electrode 4a for a biosensor) includes the insulating substrate 23 and the electrode 1 for an electrochemical measurement apparatus that is provided on a surface of the insulating substrate 23.

Furthermore, as shown in FIG. 4, the working electrode 25a (the electrode 4a for a biosensor) includes the immobilized enzyme layer 6 (or an immobilized antibody layer) that is provided above the electrode 1 for an electrochemical measurement apparatus in FIG. 4.

Moreover, the working electrode 25a includes the binder layer 24 that is provided between the electrode 1 for an electrochemical measurement apparatus and the immobilized enzyme layer 6 and is formed on the insulating substrate 23 and the electrode 1 for an electrochemical measurement apparatus so as to cover the electrode 1 for an electrochemical measurement apparatus.

The immobilized enzyme layer 6 is provided on the binder layer 24.

The electrode 1 for an electrochemical measurement apparatus, the immobilized enzyme layer 6, and the binder layer 24 constitute an electrode portion 10.

The insulating substrate 23 is a member for holding the electrode portion 10. It is preferable for the insulating substrate 23 to be formed of a material that has high water resistance, high heat resistance, high chemical resistance, excellent insulating properties, and high adhesiveness to the electrode 1 for an electrochemical measurement apparatus.

Examples of the materials that meet those requirements include ceramic, glass, quartz, and plastic.

The binder layer 24 is provided for improving the adhesiveness (bonding) between the immobilized enzyme layer 6 and the insulating substrate 23 and between the immobilized enzyme layer 6 and the electrode 1 for an electrochemical measurement apparatus.

Additionally, the binder layer 24 serves to improve the wettability of a surface of the insulating substrate 23 and to improve the uniformity of the film thickness of the immobilized enzyme layer 6 when the immobilized enzyme layer 6 is formed.

Examples of a material for the binder layer 24 include a silane coupling agent.

Examples of the silane coupling agent include aminosilanes, vinylsilanes, and epoxysilanes. In view of the adhesiveness, it is more preferable to use γ-aminopropyltriethoxysilane, which is one kind of aminosilanes.

For example, the binder layer 24 can be formed on the insulating substrate 23 and the electrode 1 for an electrochemical measurement apparatus by spin-coating a solution of a silane coupling agent.

At that time, it is preferable to adjust the concentration of the silane coupling agent at about 1 v/v % (volume/volume %). With such a concentration, an alkoxyl group can sufficiently hydrate so as to exhibit sufficient adhesiveness.

In FIG. 4, one electrode portion 10 is provided on one insulating substrate 23. However, a plurality of electrode portions 10 may be provided on one insulating substrate 23.

Furthermore, the counter electrode 7 and the reference electrode 5 are provided on separate insulating substrates 23 in FIG. 3. However, all of the electrodes may be formed on one insulating substrate 23.

Here, a method of manufacturing the working electrode 25a will be described briefly.

First, an electrode 1 for an electrochemical measurement apparatus is provided on an insulating substrate 23 by using a vapor deposition method, a sputtering method, or the like.

Next, a binder layer 24 is provided on the insulating substrate 23 and the electrode 1 for an electrochemical measurement apparatus so as to cover the electrode 1 for an electrochemical measurement apparatus by spin-coating.

Thereafter, an enzyme solution, a crosslinking agent of protein such as glutaraldehyde, and a solution containing albumin are dropped onto the binder layer 24 to form an immobilized enzyme layer 6. Thus, a working electrode 25a is completed.

A method of measuring the concentration of the measurement target substance in the solution 15a with the biosensor 3b is the same as that of the second embodiment, and the explanation thereof is omitted herein.

Thus, according to the third embodiment, the biosensor 3b includes the working electrode 25a, the counter electrode 7, the reference electrode 5, and the measurement equipment 13a. The electrode 1 for an electrochemical measurement apparatus in the working electrode 25a employs an alloy containing iridium and rhenium with such a composition that the selectivity for hydrogen peroxide can be obtained.

Accordingly, it is possible to obtain the same advantages as in the second embodiment.

Furthermore, according to the third embodiment, the working electrode 25a has a structure in which the electrode 1 for an electrochemical measurement apparatus is provided on the insulating substrate 23 with the binder layer 24 being provided between the electrode 1 for an electrochemical measurement apparatus and the immobilized enzyme layer 6.

Therefore, the adhesiveness (bonding) between the immobilized enzyme layer 6 and the electrode 1 for an electrochemical measurement apparatus can be improved as compared to the second embodiment. Furthermore, it is possible to improve the uniformity of the film thickness of the immobilized enzyme layer 6 when the immobilized enzyme layer 6 is formed.

EXAMPLES

Next, the present invention will be described in greater detail based on specific examples.

Example 1

An electrochemical measurement apparatus 3 shown in FIG. 1 was produced. A current ratio of hydrogen peroxide to ascorbic acid, which is one of interference substances, was calculated by constant-potential measurement in a solution containing hydrogen peroxide and interference substances. Thus, the selectivity of the working electrode 9 for hydrogen peroxide was evaluated.

First, the working electrode 9 (the electrode 1 for an electrochemical measurement apparatus) was produced as follows.

First of all, an iridium wire and a rhenium wire were prepared. Iridium-rhenium alloys were produced by arc-melting method.

The iridium-rhenium alloys produced included six types of alloys in which an atom weight ratio of iridium and rhenium was 100:0, 99:1, 90:10, 55:45, 10:90, and 0:100, respectively.

Next, each of the produced iridium-rhenium alloys was fixed on a flexible substrate having a printed circuit by an adhesive. Wiring was conducted by wire bonding. Then a waterproof treatment was performed with a silicone sealing agent. Thus, the working electrode 9 (the electrode 1 for an electrochemical measurement apparatus) was completed.

The working electrode 9 had an electrode area of $59.0 \times 10^{-6}$ m$^2$ to $71.4 \times 10^{-6}$ m$^2$ (59.0 mm$^2$ to 71.4 mm$^2$)

Next, an existing glass composite electrode (GST-5741C made by DKK-TOA Corporation) was prepared as the reference electrode 5, and an existing platinum electrode (002233 made by BAS Inc.) was prepared as the counter electrode 7.

Thereafter, N-Tris(hydroxyl-methyl)-methyl-2-aminoethanesulfonic acid of 100 mol/m$^3$ (100 mM) (a pH buffer solution made by Dojindo Laboratories, which included sodium chloride of 150 mol/m$^3$ (150 mM) with the pH being adjusted at 7 and which is hereinafter referred to as TES) was prepared as the solution 15. The working electrode 9, the reference electrode 5, and the counter electrode 7 were immersed in a 0.1-liter beaker including the solution 15. Those electrodes were connected to the measurement equipment 13 through the wires 11. Thus, the electrochemical measurement apparatus 3 was produced.

For constant-potential measurement to hydrogen peroxide and ascorbic acid, response currents were measured when potentials of 0.5 V, 0.7 V, and 0.9 V were respectively applied.

The measurement used a difference between a current at a steady state after each potential was applied and a response current obtained when hydrogen peroxide and ascorbic acid were added.

A current ratio of hydrogen peroxide to ascorbic acid (interference substance) at the time of each application was calculated. The results are shown in FIG. 5.

Figure 5:
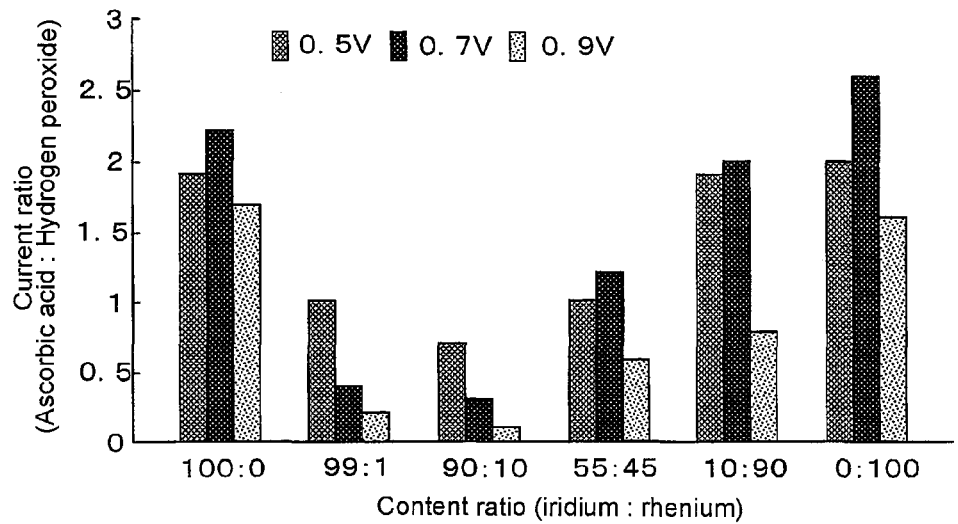
FIG. 5 is a graph showing experimental results of Example 1.

As shown in FIG. 5, a response current to hydrogen peroxide was produced selectively when the atom weight ratio of iridium and rhenium was 99:1, 90:10, and 55:45.

Particularly, a response current to hydrogen peroxide was produced selectively when the atom weight ratio of iridium and rhenium was 99:1 and 90:10 (when the ratio of rhenium to iridium was in a range of 1 atom weight % to 10 atom weight %).

Specifically, it can be seen that an alloy with the aforementioned compositional range selectively oxidizes hydrogen peroxide and thus has high oxidizability to hydrogen peroxide but low oxidizability to ascorbic acid.

On the other hand, when the atom weight ratio of iridium and rhenium was 100:0, 10:90, and 0:100, the oxidizability to ascorbic acid was equivalent to that to hydrogen peroxide. Thus, the working electrode 9 was influenced by the interference substance.

Example 2

Evaluation of uric acid and acetaminophen as interference substances was conducted under the same conditions as in Example 1 expect that only 0.7 V was used for an application potential for evaluation.

Figure 6:
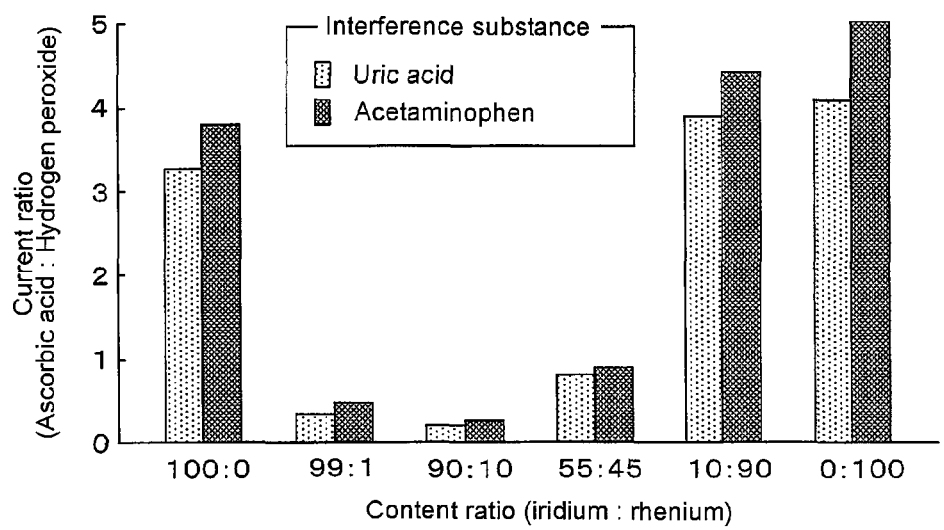
FIG. 6 is a graph showing experimental results of Example 2.

The results are shown in FIG. 6.

As shown in FIG. 6, the electrode of an iridium-rhenium alloy in this example had a low oxidizability to uric acid and acetaminophen similarly to ascorbic acid and selectively oxidized hydrogen peroxide when the atom weight ratio of iridium and rhenium was 99:1, 90:10, and 55:45.

Furthermore, the effects of selective oxidation of hydrogen peroxide were the most significant when a ratio of rhenium to iridium was 10 atom weight %.

Example 3

A biosensor 3a shown in FIG. 2 was produced as a biosensor for measuring glucose. The concentration of glucose in a solution 15a containing ascorbic acid and glucose at a known concentration was measured. Thus, the selectivity of the working electrode 25a for hydrogen peroxide was evaluated.

First, an electrode 1 of an iridium-rhenium alloy for an electrochemical measurement apparatus was produced in the same manner as in Example 1 so that the atom weight ratio of iridium and rhenium was 90:10.

Next, γ-aminopropyltriethoxysilane of 1 v/v % (made by Shin-Etsu Chemical Co., Ltd.) was applied onto a surface of the produced electrode 1 for an electrochemical measurement apparatus. Then the electrode was heated at 110° C. for one hour.

After completion of the heating, a bovine serum albumin solution adjusted at 22.5 w/v % with TES of 100 mol/m$^3$ (100 mM), which included glutaraldehyde of 1 v/v % and glucose oxidase of 56.5 U$\times 10^{-6}$/liter (56.5 U/µl), was similarly applied. The electrode was dried in a refrigerator at 2.5±1° C. for 24 hours. Thus, a working electrode 9a (an electrode 4a for a biosensor) was produced.

Furthermore, the reference electrode 5 and the counter electrode 7 were also prepared. Those electrodes were immersed in the solution 15a. Those electrodes were connected to the measurement equipment 13a through the wires 11. Thus, the biosensor 3a was produced.

An electrode for a biosensor in which platinum was used for the working electrode instead of the iridium-rhenium alloy was produced as a comparative example. A biosensor using this electrode was produced.

Lyphochek Urine Control made by Bio-Rad Laboratories, Inc. was used as the solution 15a. Ascorbic acid was added to be $50 \times 10^{-5}$ kg/liter (50 mg/dl), and glucose was added to be $10 \times 10^{-5}$ kg/liter (10 mg/dl).

Subsequently, a calibration curve of the biosensor 3a was generated with glucose solutions of $0 \times 10^{-5}$, $5 \times 10^{-5}$, $10 \times 10^{-5}$, and $20 \times 10^{-5}$ kg/liter (0, 5, 10, and 20 mg/dl). The concentration of glucose in the control urine was measured.

Measurements were repeated three times with a constant potential of 0.9 V.

As a result, the biosensor 3a using the electrode of an iridium-rhenium alloy exhibited $10.8 \pm 0.3 \times 10^{-5}$ kg/liter (10.8±0.3 mg/dl), and the biosensor using the platinum electrode exhibited $30.1 \pm 3.6 \times 10^{-5}$ kg/liter (30.1±3.6 mg/dl).

The biosensor 3a using the iridium-rhenium alloy of this example could measure substantially the exact concentration of glucose. However, the biosensor using the platinum electrode of the comparative example could not measure the exact concentration of glucose because of interference caused by an oxidation current of ascorbic acid.

Example 4

The biosensor 3a used in Example 3 was prepared.

The electrodes of the biosensor 3a were immersed in a TES solution under a room temperature. Glucose of $10 \times 10^{-5}$ kg/liter (10 mg/dl) and ascorbic acid of $1 \times 10^{-5}$ kg/liter (1 mg/dl) were measured every a certain days. Thus, the stability of the electrodes was evaluated.

For evaluation, a ratio of a current value for ascorbic acid to a current value for hydrogen peroxide was calculated when an applied potential was 0.9 V.

Figure 7:
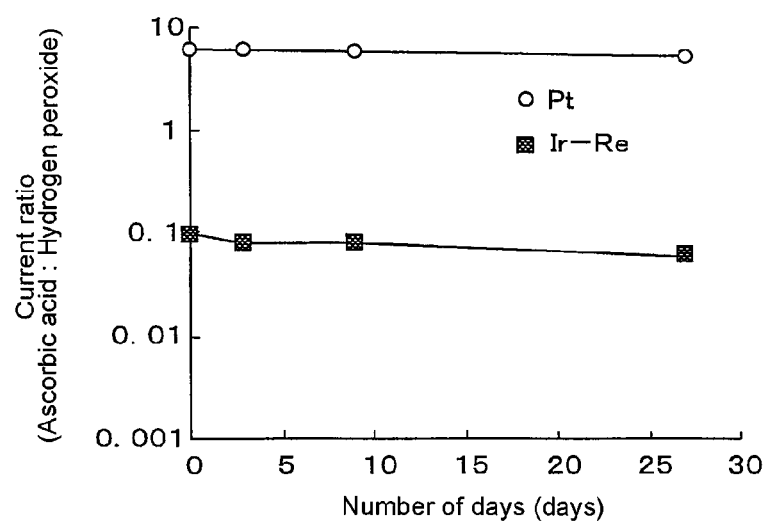
FIG. 7 is a graph showing experimental results of Example 4.

The results are shown in FIG. 7.

In the graph of FIG. 7, "Pt" shows measured values of a biosensor using a platinum electrode (comparative example), whereas "Ir—Re" shows measured values of a biosensor 3a using an iridium-rhenium alloy electrode (this example).

As shown in FIG. 7, the biosensor using a platinum electrode exhibited a higher current for ascorbic acid than for hydrogen peroxide. The current ratio was in a range of 5.5 to 6.1 (ascorbic acid/hydrogen peroxide) and remained stable for 27 days.

On the other hand, the biosensor 3a using an iridium-rhenium alloy electrode exhibited a current selectively for hydrogen peroxide generated from glucose and hardly exhibited a current for ascorbic acid.

The current ratio was in a range of 0.06 to 0.1 (ascorbic acid/hydrogen peroxide) and hardly varied for 27 days. Thus, the current ratio remained stable.

Example 5

An immunological sensor using a working electrode in which an immobilized antibody layer was provided instead of the immobilized enzyme layer 6 in Example 3 was prepared. The concentration of chorionic gonadotropin in a solution containing ascorbic acid and chorionic gonadotropin at a known concentration was measured. Thus, the selectivity of the working electrode for hydrogen peroxide was evaluated.

The working electrode was produced as follows.

First, an electrode 1 for an electrochemical measurement apparatus was produced in the same manner as in Example 1 so that the atom weight ratio of iridium and rhenium was 90:10.

The produced electrode 1 for an electrochemical measurement apparatus was immersed in a solution of a human chorionic gonadotropin antibody (a mouse immune monoclonal antibody made by HyTest Ltd.) of $1 \times 10^{-3}$ kg/0.2 liter (1 mg/0.2 ml) for one hour.

After the immersion, the electrode 1 was further immersed in 1,3-diaminobenzene of 3 mol/m$^3$ (3 mM), made by Sigma-Aldrich Corporation, U.S.A., which included a phosphate buffer solution having a pH of 7.4 and sodium chloride of $0.1 \times 10^3$ mol/m$^3$ (0.1 M). The electrode 1 was swept 100 times between 0 V to 0.8 V at $2 \times 10^{-3}$ V/s (2 mV/s). Then a potential of 0.65 V was applied for five hours. Thereafter, the electrode 1 was immersed in a polyvinyl alcohol of 1 w/v % for one hour to thereby immobilize the aforementioned antibody.

As a comparative example, the same type of antibody was immobilized on an electrode using platinum by the same process.

Lyphochek Urine Control made by Bio-Rad Laboratories, Inc. was used as the solution. Ascorbic acid (made by Wako Pure Chemical Industries, Ltd.) and chorionic gonadotropin (a human-pregnancy-urine-derived β subunit made by AspenBio Pharma, Inc.) were added so that their final concentrations were $50 \times 10^{-5}$ kg/liter (50 mg/dl) and $60 \times 10^{-6}$ mol/m$^3$ (60 nM), respectively.

Subsequently, calibration curves of the immunological sensors of this example and the comparative example were generated with a chorionic gonadotropin solution of $0 \times 10^{-6}$, $66 \times 10^{-6}$, and $132 \times 10^{-6}$ mol/m$^3$ (0, 66, and 132 nM). The concentration of chorionic gonadotropin in the solution was measured. Measurements were repeated three times in a sweeping range of 0.1 V to 1.2 V by a square wave voltammetry method with a pulse potential of $40 \times 10^{-3}$ V (40 mV), a frequency of 4 Hz, and a step potential of $10 \times 10^{-3}$ V (10 mV).

As a result, the immunological sensor using the electrode of the iridium-rhenium alloy exhibited $61.1 \pm 0.6 \times 10^{-6}$ mol/m$^3$ ($61.1 \pm 0.6$ nM) at 1.1 V. The immunological sensor using the platinum electrode exhibited $118 \pm 12.2 \times 10^{-6}$ mol/m$^3$ ($118 \pm 12.2$ nM).

The immunological sensor including the working electrode using the iridium-rhenium alloy of this example could measure substantially the exact concentration of chorionic gonadotropin. However, the immunological sensor including the working electrode using the platinum electrode of the comparative example could not measure the exact concentration because of interference caused by an oxidation current of ascorbic acid.

Thus, the electrode 1 for an electrochemical measurement apparatus according to this example could eliminate influence from interference substances even if it was used for an immunological sensor.

In the aforementioned embodiments and examples, the biosensor 3a and the immunological sensor are applied primarily to sensors for measuring the concentration of glucose or chorionic gonadotropin in a solution. However, the present invention is not limited to those examples. The present invention is applicable to measurement of the concentration of any measurement target substances that can be converted into hydrogen peroxide by a catalytic reaction.

This application claims the benefit of priority from Japanese patent application No. 2007-289836, filed on Nov. 7, 2007, the disclosure of which is incorporated herein in its entirety by reference.

The invention claimed is:

1. A detection apparatus for detecting a concentration of hydrogen peroxide in a solution, comprising an electrode for an electrochemical measurement apparatus that is formed of an alloy containing at least iridium and rhenium with such a composition that selectivity for hydrogen peroxide can be obtained,
   wherein an atom weight ratio of iridium and rhenium in the alloy is in a range of from 99:1 to 90:10.

2. An electrode for a biosensor to detect a measurement target substance in a solution, wherein an immobilized enzyme layer and/or an immobilized antibody layer is provided on a surface of the electrode for an electrochemical measurement apparatus that is formed of an alloy containing at least iridium and rhenium with such a composition that selectivity for hydrogen peroxide can be obtained,
   wherein an atom weight ratio of iridium and rhenium in the alloy is in a range of from 99:1 to 90:10.

3. The electrode for a biosensor as recited in claim 2, wherein the immobilized enzyme layer includes at least one kind of enzyme that can convert the measurement target substance into hydrogen peroxide, and
   the electrode for an electrochemical measurement apparatus detects the hydrogen peroxide converted by the immobilized enzyme layer for thereby detecting the measurement target substance.

4. The electrode for a biosensor as recited in claim 3, wherein the enzyme comprises at least one of lactate oxidase, glucose oxidase, uric acid oxidase, urea oxidase, alcohol oxidase, creatininase, creatinase, and sarcosine oxidase.

5. The electrode for a biosensor as recited in claim 2, wherein the immobilized antibody layer includes at least one kind of antibody that can react with the measurement target substance, and
   the electrode detects a current produced by a reaction between the antibody in the immobilized antibody layer and the measurement target substance for thereby detecting the measurement target substance.

6. The electrode for a biosensor as recited in claim 5, wherein the antibody comprises a human chorionic gonadotropin antibody.

7. The electrode for a biosensor as recited in claim 2, further comprising:
- an insulating substrate for holding the electrode for an electrochemical measurement apparatus; and
- a binder layer between the electrode for an electrochemical measurement apparatus and the immobilized enzyme layer and/or the immobilized antibody layer, the binder layer being provided on the insulating substrate and the electrode for an electrochemical measurement apparatus so as to cover the electrode for an electrochemical measurement apparatus.

8. A biosensor for measuring a concentration of a measurement target substance in a solution, comprising the electrode for a biosensor as recited in claim 2.

9. The detection apparatus as recited in claim 1, wherein the electrode for an electrochemical measurement apparatus serves as a working electrode.

10. The detection apparatus as recited in claim 9, comprising a reference electrode and a counter electrode.

11. The detection apparatus as recited in claim 10, wherein the reference electrode is one of a silver electrode and a silver chloride electrode.

12. The detection apparatus as recited in claim 1, comprising a device for performing a current-potential measurement or a constant-potential measurement.

13. The biosensor as recited in claim 8, wherein the electrode for a biosensor serves as a working electrode, and a concentration of a measurement target substance in a solution is detected by performing an electrochemical measurement.

14. The biosensor as recited in claim 13, comprising a reference electrode and a counter electrode.

15. The biosensor as recited in claim 14, wherein the reference electrode is one of a silver electrode and a silver chloride electrode.

16. The biosensor as recited in claim 8, comprising a device for performing a current-potential measurement or a constant-potential measurement.

* * * * *